(12) United States Patent
Liang et al.

(10) Patent No.: US 10,343,988 B1
(45) Date of Patent: Jul. 9, 2019

(54) HYDROXYTYROSOL THIODIPROPIONIC ACID ESTER WITH ANTIOXIDANT ACTIVITY AND A METHOD OF PREPARING THE SAME

(71) Applicants: Chengyuan Liang, Xi'an (CN); Lei Tian, Xi'an (CN); Danni Tian, Xi'an (CN); Yuzhi Liu, Xi'an (CN); Xingke Ju, Xi'an (CN); Nan Hui, Xi'an (CN); Mi Wu, Xi'an (CN); Juan Li, Xi'an (CN); Han Li, Xi'an (CN); Bin Tian, Xi'an (CN); Qianqian Zhao, Xi'an (CN)

(72) Inventors: Chengyuan Liang, Xi'an (CN); Lei Tian, Xi'an (CN); Danni Tian, Xi'an (CN); Yuzhi Liu, Xi'an (CN); Xingke Ju, Xi'an (CN); Nan Hui, Xi'an (CN); Mi Wu, Xi'an (CN); Juan Li, Xi'an (CN); Han Li, Xi'an (CN); Bin Tian, Xi'an (CN); Qianqian Zhao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/359,988

(22) Filed: Mar. 20, 2019

(51) Int. Cl.
*C07C 323/56* (2006.01)
*C07C 319/20* (2006.01)
*C09K 15/14* (2006.01)

(52) U.S. Cl.
CPC .......... *C07C 323/56* (2013.01); *C07C 319/20* (2013.01); *C09K 15/14* (2013.01)

(58) Field of Classification Search
CPC .......................... C07C 323/56; C07C 319/20
See application file for complete search history.

(56) References Cited

FOREIGN PATENT DOCUMENTS

GB     1212466    * 11/1970

* cited by examiner

*Primary Examiner* — Jafar F Parsa

(57) ABSTRACT

A compound having the following formula I:

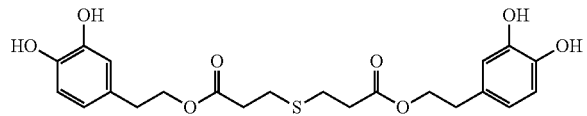

is disclosed. A method of preparing the compound of formula I is also disclosed.

12 Claims, 3 Drawing Sheets

HYDROXYTYROSOL THIODIPROPIONIC ACID ESTER WITH ANTIOXIDANT ACTIVITY AND A METHOD OF PREPARING THE SAME

The present invention claims priority to Chinese Patent Application No.: 201910153112.3, filed on Mar. 1, 2019, which is incorporated by reference for all purposes as if fully set forth herein.

FIELD OF THE INVENTION

The present invention relates to food and cosmetic additives, in particular, to a hydroxytyrosol thiodipropionic acid ester having antioxidant activity and a method of preparing the same.

BACKGROUND OF THE INVENTION

Oxidation is the main cause of food spoilage. During storage and transportation, foods are spoiled and degraded by microorganisms. Foods also chemically react with oxygen in the air, causing them, especially oils or fats, to deteriorate. This not only reduces food nutrition, but also deteriorates flavor and color. This also produces harmful substances that endanger human health. Therefore, adding an appropriate amount of antioxidants to foods is a simple and economical method to prevent oxidative deterioration of foods.

The use of antioxidants not only prolongs the storage period and the shelf life of foods, but also brings good economic benefits to producers and distributors and gives consumers a better sense of security. At present, synthetic and semi-synthetic antioxidants have attracted more and more attentions. In addition to being used alone, the antioxidants can also be used with other food additives having other functions to form a multifunctional preparation and a dosage form, for example, packaging materials with preservatives and antioxidants.

Hydroxytyrosol (4-(2-hydroxyethyl)-1,2-benzenediol; compound of formula II) is a phenylethanoid, a type of phenolic phytochemical with antioxidant properties in vitro. In nature, hydroxytyrosol is found in olive leaf and olive oil, in the form of its elenolic acid ester oleuropein and, especially after degradation, in its plain form.

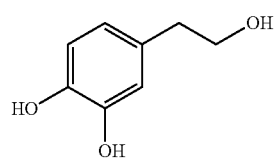

Thiodipropionic acid (3,3'-thiodipropionic acid; the compound of formula III) can effectively decompose the hydroperoxide in the automatic oxidation chain reaction of oil, thereby interrupting the chain reaction and improving the shelf life of oil. Thiodipropionic acid has not yet been included in China's food additive health standards (GB2760-2014), and its research on food, medicine, and health care products is lacking.

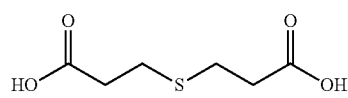

SUMMARY OF THE INVENTION

In one embodiment, the present invention provides a compound having the following formula I:

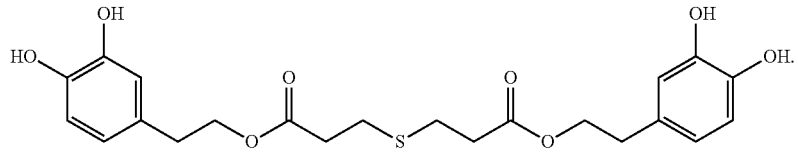 [SMILES: O=C(CCSCCC(=O)OCCc1ccc(O)c(O)c1)OCCc1ccc(O)c(O)c1]

In another embodiment, the present invention provides a method of preparing the compound of formula I. The method includes reacting the compound of formula II with the compound of formula III to obtain the compound of formula I:

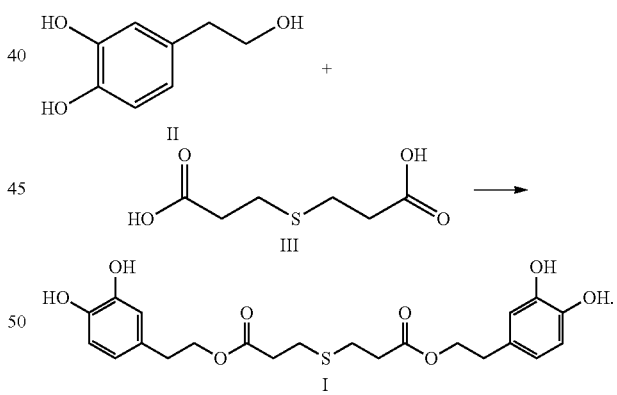

In another embodiment, the reaction of the compound of formula II with the compound of formula III includes the following steps: dissolving the compound of formula II and the compound of formula III in an organic solvent to form a reaction mixture under nitrogen atmosphere; adding a dehydrating agent to the reaction mixture; heating the reaction mixture at 50-60° C. for 8-10 hours under sonication; removing the organic solvent from the reaction mixture to obtain a crude product; and purifying the crude product on a microporous resin with a mixture of methanol and water as an eluent.

In another embodiment, the organic solvent is acetonitrile, THF (tetrahydrofuran), or DMF (dimethylformamide).

In another embodiment, the organic solvent is DMF.

In another embodiment, the molar ratio of the compound of formula II and the compound of formula III is 2:1 to 2.2:1.

In another embodiment, the molar ratio of the compound of formula II and the compound of formula III is 2.2:1.

In another embodiment, the dehydrating agent is DCC (N,N'-dicyclohexylcarbodiimide), concentrated sulfuric acid, or EDC (1-ethyl-3-(3-dimethylaminopropyl)carbodiimide).

In another embodiment, the dehydrating agent is DCC.

In another embodiment, the reaction mixture is heated at 60° C.

In another embodiment, the reaction mixture is heated for 8 hours.

In another embodiment, the mixture of methanol and water has a volume ratio of 1:1.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
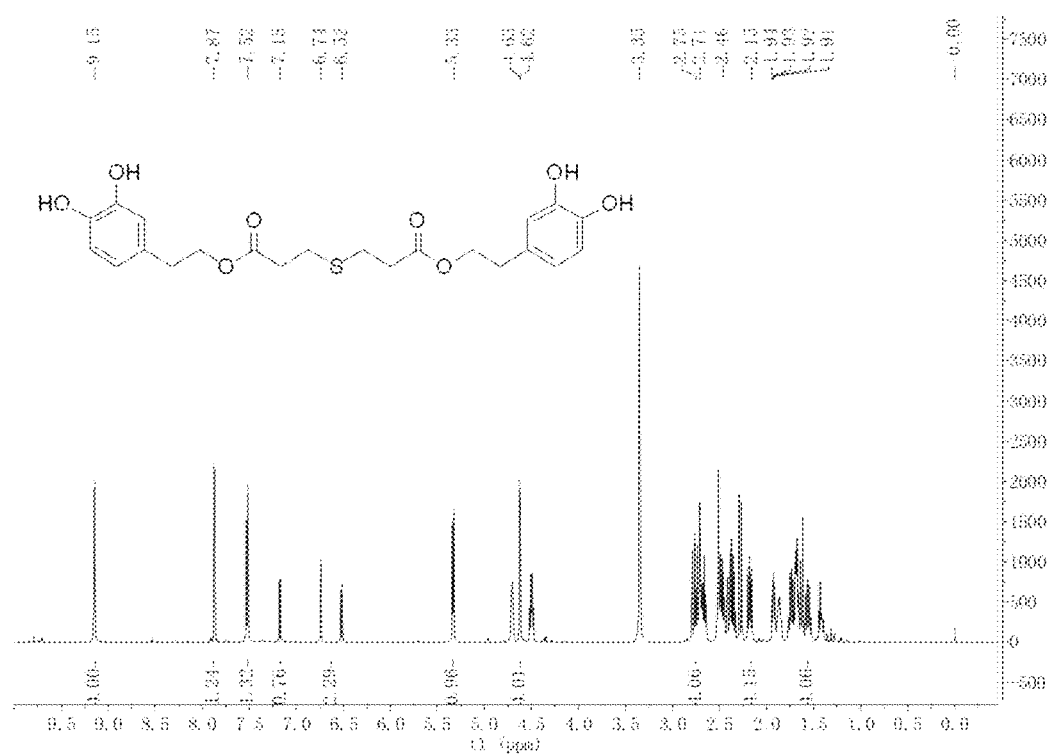
FIG. 1 is the $^1$HNMR spectrum of the hydroxytyrosol thiodipropionic acid ester.
Figure 2:
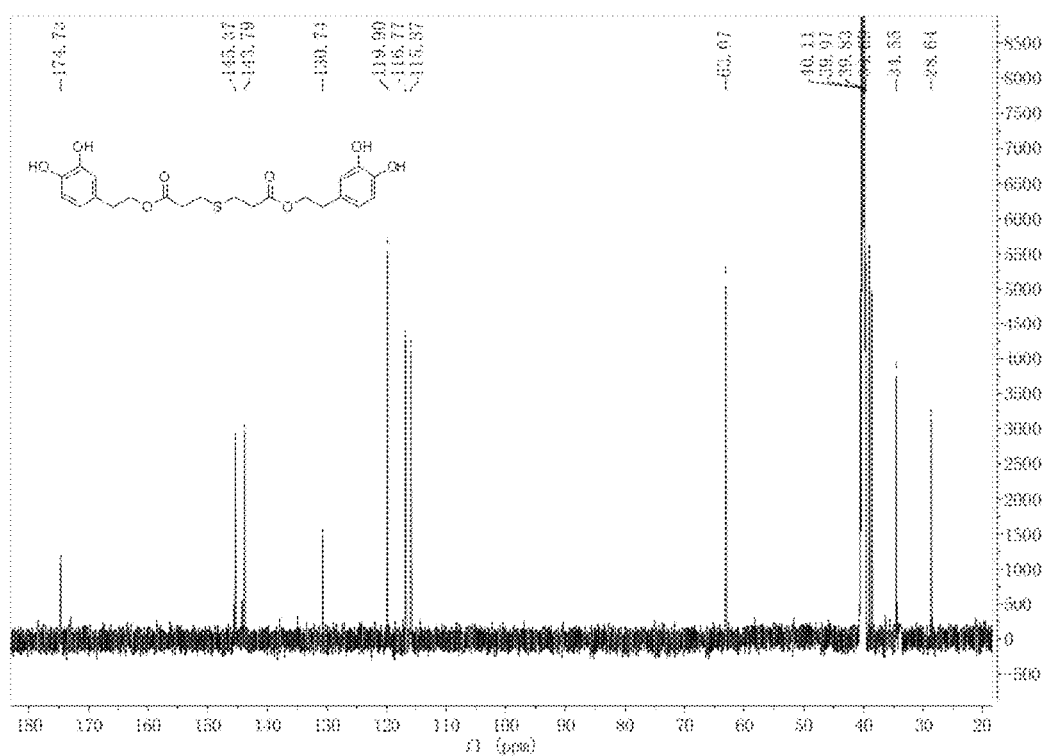
FIG. 2 is the $^{13}$CNMR spectrum of the hydroxytyrosol thiodipropionic acid ester.

Reference will now be made in detail to embodiments of the present invention, example of which is illustrated in the accompanying drawings. The following examples illustrate the present invention, but the present invention is not limited to the following examples.

In the present invention, hydroxytyrosol is structurally modified by reacting with thiodipropionic acid to obtain a hydroxytyrosol thiodipropionic acid ester. The synthesis method of the hydroxytyrosol thiodipropionic acid ester is described. The antioxidant activity is also measured. The hydroxytyrosol thiodipropionic acid ester can be used as a new type of antioxidant additive for food, medicine and health care products.

Example 1

Preparation of Hydroxytyrosol Thiodipropionic Acid Ester (bis(3,4-dihydroxyphenethyl) 3,3'-thiodipropanoate) (Formula I)

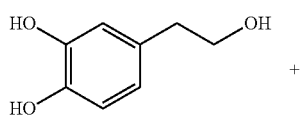

+

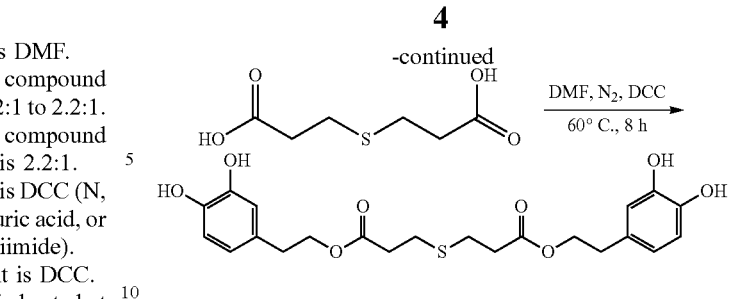

95 mg (0.62 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 115 mg (0.56 mmol) DCC was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:1) mixture. The elution was collected and concentrated to obtain 73.6 mg of purified hydroxytyrosol thiodipropionic acid ester, a yield of 58.4%.

$^1$H-NMR (400 MHz, DMSO-$d_6$) δ (ppm): 9.15 (4H, s), 7.87 (1H, s), 7.52 (1H, d), 7.18 (1H, d), 6.74~6.52 (2H, m), 5.33 (1H, d), 4.63~4.62 (4H, m), 2.75~2.71 (4H, m), 2.15 (4H, m), 1.94~1.91 (4H, m); $^{13}$C-NMR (75 MHz, DMSO-$d_6$) δ (ppm): 174.73, 145.37, 143.79, 130.74, 119.90, 116.77, 115.87, 63.07, 34.55, 28.64; MS (ESI) for (M+H)$^+$: 451.1.

Example 2

Preparation of Hydroxytyrosol Thiodipropionic Acid Ester (bis(3,4-dihydroxyphenethyl) 3,3'-thiodipropanoate)

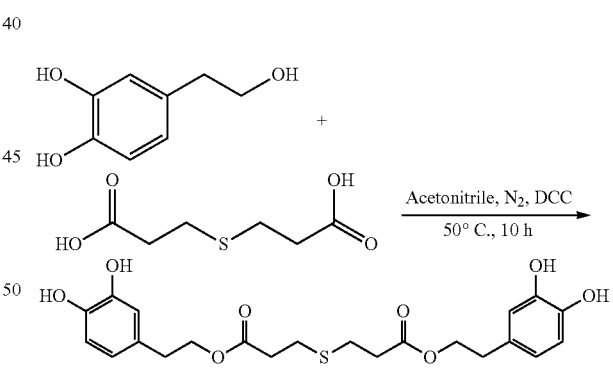

95 mg (0.62 mmol) hydroxytyrosol and 50 mg (0.28 mmol) 3,3'-thiodipropionic acid were placed in a 100 mL reactor. 50 mL acetonitrile was added to form a reaction mixture under nitrogen atmosphere. 115 mg (0.56 mmol) DCC was then added to the reaction mixture. The reaction mixture was heated at 50° C. under sonication and nitrogen atmosphere for 10 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (2:1) mixture. The elution was collected and concentrated to obtain 55.1 mg of purified hydroxytyrosol thiodipropionic acid ester, a yield of 43.7%.

Example 3

Preparation of Hydroxytyrosol Thiodipropionic Acid Ester (bis(3,4-dihydroxyphenethyl) 3,3'-thiodipropanoate)

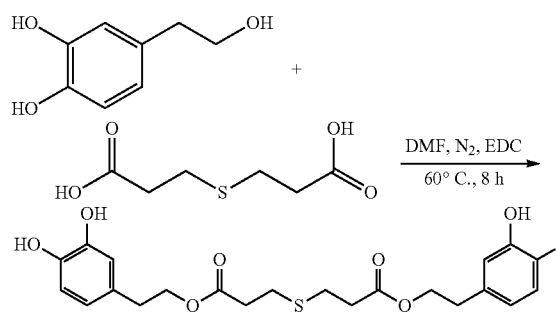

95 mg (0.62 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 110 mg (0.6 mmol) EDC was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:2) mixture. The elution was collected and concentrated to obtain 49.2 mg of purified hydroxytyrosol thiodipropionic acid ester, a yield of 39.0%.

Example 4

Preparation of Hydroxytyrosol Thiodipropionic Acid Ester (bis(3,4-dihydroxyphenethyl) 3,3'-thiodipropanoate)

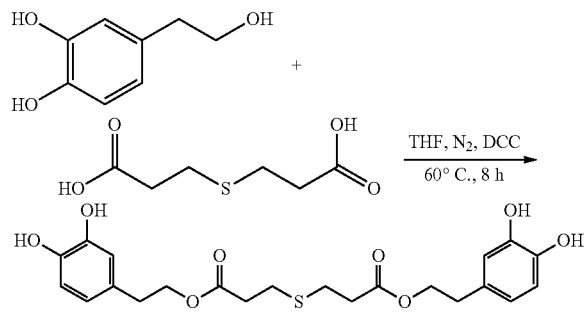

95 mg (0.62 mmol) hydroxytyrosol and 50 mg (0.28 mmol) 3,3'-thiodipropionic acid were placed in a 100 mL reactor. 50 mL THF was added to form a reaction mixture under nitrogen atmosphere. 115 mg (0.56 mmol) DCC was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (2:1) mixture. The elution was collected and concentrated to obtain 58.6 mg of purified hydroxytyrosol thiodipropionic acid ester, a yield of 46.5%.

Example 5

Preparation of Hydroxytyrosol Thiodipropionic Acid Ester (bis(3,4-dihydroxyphenethyl) 3,3'-thiodipropanoate)

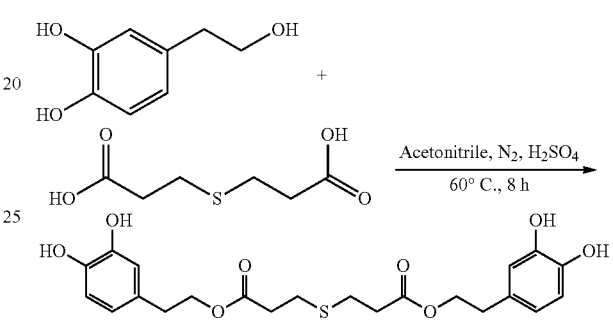

95 mg (0.62 mmol) hydroxytyrosol and 50 mg (0.28 mmol) 3,3'-thiodipropionic acid were placed in a 100 mL reactor. 50 mL acetonitrile was added to form a reaction mixture under nitrogen atmosphere. 5 mL concentrated sulfuric acid was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:1) mixture. The elution was collected and concentrated to obtain 40.7 mg of purified hydroxytyrosol thiodipropionic acid ester, a yield of 32.3%.

Example 6

Preparation of Hydroxytyrosol Thiodipropionic Acid Ester (bis(3,4-dihydroxyphenethyl) 3,3'-thiodipropanoate)

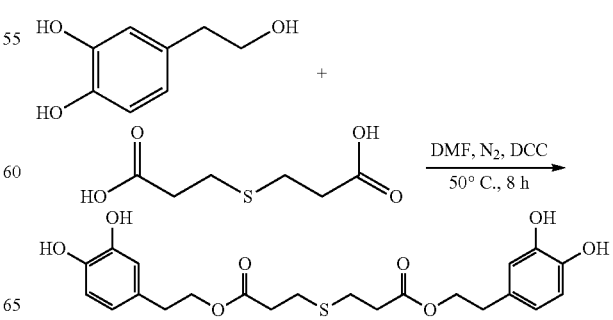

95 mg (0.62 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 115 mg (0.56 mmol) DCC was then added to the reaction mixture. The reaction mixture was heated at 50° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using an HP-20 microporous resin column and eluting with methanol. The elution was collected and concentrated to obtain 38.6 mg of purified hydroxytyrosol thiodipropionic acid ester, a yield of 30.6%.

Example 7

Preparation of Hydroxytyrosol Thiodipropionic Acid Ester (bis(3,4-dihydroxyphenethyl) 3,3'-thiodipropanoate)

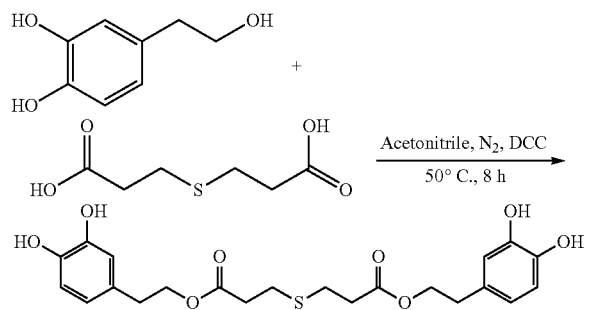

95 mg (0.62 mmol) hydroxytyrosol and 50 mg (0.28 mmol) 3,3'-thiodipropionic acid were placed in a 100 mL reactor. 50 mL acetonitrile was added to form a reaction mixture under nitrogen atmosphere. 57.8 mg (0.28 mmol) DCC was then added to the reaction mixture. The reaction mixture was heated at 50° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using an XAD-2 microporous resin column and eluting with methanol and water (4:1) mixture. The elution was collected and concentrated to obtain 52.7 mg of purified hydroxytyrosol thiodipropionic acid ester, a yield of 41.8%.

Example 8

Preparation of Hydroxytyrosol Thiodipropionic Acid Ester (bis(3,4-dihydroxyphenethyl) 3,3'-thiodipropanoate)

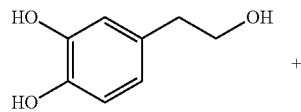

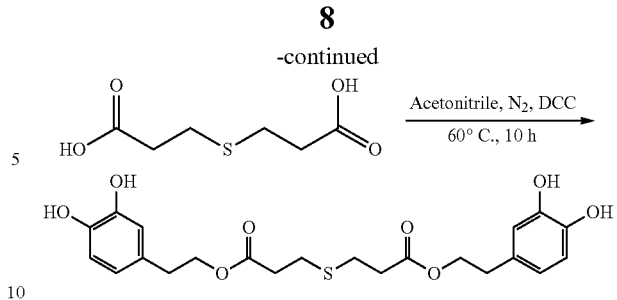

86 mg (0.56 mmol) hydroxytyrosol and 50 mg (0.28 mmol) 3,3'-thiodipropionic acid were placed in a 100 mL reactor. 50 mL acetonitrile was added to form a reaction mixture under nitrogen atmosphere. 115 mg (0.56 mmol) DCC was then added to the reaction mixture. The reaction mixture was heated at 60° C. under sonication and nitrogen atmosphere for 10 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:1) mixture. The elution was collected and concentrated to obtain 66.9 mg of purified hydroxytyrosol thiodipropionic acid ester, a yield of 53.1%.

Example 9

Preparation of Hydroxytyrosol Thiodipropionic Acid Ester (bis(3,4-dihydroxyphenethyl) 3,3'-thiodipropanoate)

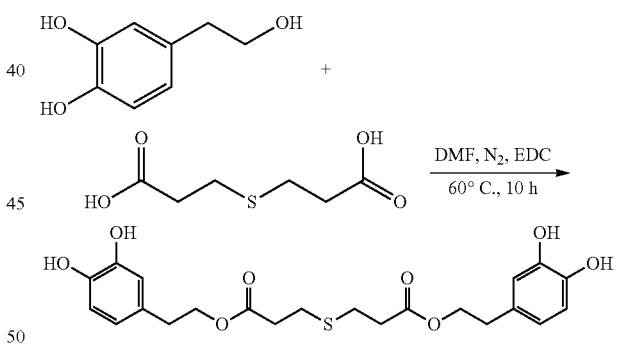

95 mg (0.62 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 106 mg (0.56 mmol) EDC was then added to the reaction mixture. The reaction mixture was heated at 60° C. under sonication and nitrogen atmosphere for 10 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:1) mixture. The elution was collected and concentrated to obtain 57.0 mg of purified hydroxytyrosol thiodipropionic acid ester, a yield of 45.2%.

Example 10

Preparation of Hydroxytyrosol Thiodipropionic Acid Ester (bis(3,4-dihydroxyphenethyl) 3,3'-thiodipropanoate)

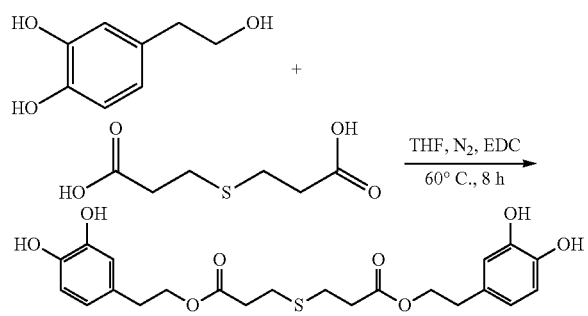

95 mg (0.62 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 106 mg (0.56 mmol) EDC was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using an HP-20 microporous resin column and eluting with methanol and water (4:1) mixture. The elution was collected and concentrated to obtain 36.2 mg of purified hydroxytyrosol thiodipropionic acid ester, a yield of 28.7%.

Example 11

Preparation of Hydroxytyrosol Thiodipropionic Acid Ester (bis(3,4-dihydroxyphenethyl) 3,3'-thiodipropanoate)

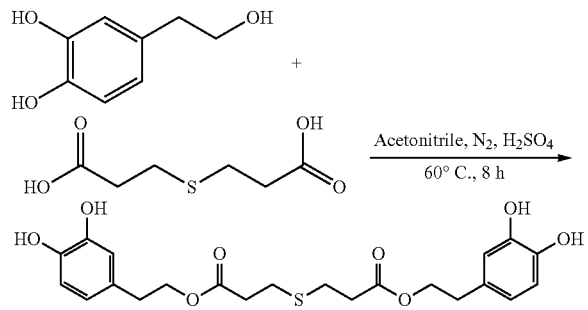

95 mg (0.62 mmol) hydroxytyrosol and 50 mg (0.28 mmol) 3,3'-thiodipropionic acid were placed in a 100 mL reactor. 50 mL acetonitrile was added to form a reaction mixture under nitrogen atmosphere. 5 mL concentrated sulfuric acid was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using an XAD-2 microporous resin column and eluting with methanol and water (1:1) mixture. The elution was collected and concentrated to obtain 45.2 mg of purified hydroxytyrosol thiodipropionic acid ester, a yield of 35.9%.

Example 12

Preparation of Hydroxytyrosol Thiodipropionic Acid Ester (bis(3,4-dihydroxyphenethyl) 3,3'-thiodipropanoate)

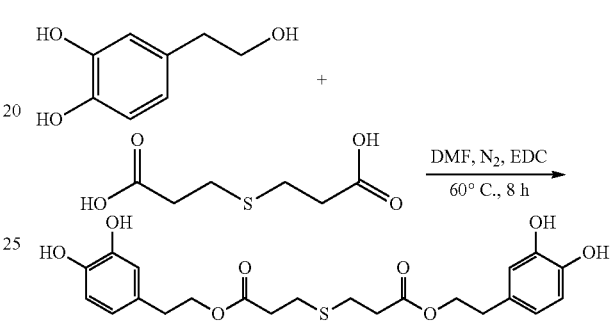

86 mg (0.56 mmol) hydroxytyrosol and 50 mg (0.28 mmol) 3,3'-thiodipropionic acid were placed in a 100 mL reactor. 50 mL DMF was added to form a reaction mixture under nitrogen atmosphere. 110 mg (0.6 mmol) EDC was then added to the reaction mixture. The reaction mixture was heated at 60° C. under sonication and nitrogen atmosphere for 8 hours. After thin layer chromatography (TLC) indicated that the reaction was complete, the reaction mixture was cooled down to room temperature, concentrated under reduced pressure to obtain a crude product. The crude product was purified by an adsorption purification process using a D-101 microporous resin column and eluting with methanol and water (1:1) mixture. The elution was collected and concentrated to obtain 48.4 mg of purified hydroxytyrosol thiodipropionic acid ester, a yield of 38.4%.

Example 13

DPPH Radical Scavenging Activity Assay

Experimental Principle:

2,2-Diphenyl-1-picryl hydrazyl (DPPH) is an organic compound composed of a stable organic radical. In the DPPH molecule, due to the presence of multiple electron-withdrawing —$NO_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Experimental Method:

(a) Preparation of DPPH solution: measuring exact amount of 2,2-diphenyl-1-picryl hydrazyl (DPPH) and dissolving in methanol to prepare a $0.2 \times 10^{-4}$ mol/L DPPH solution, stored at 0° C. in dark.

(b) Preparation of sample solutions: Vc (vitamin C, positive control), hydroxytyrosol thiodipropionic acid ester, hydroxytyrosol (control), thiodipropionic acid (control), and a mixture of hydroxytyrosol and thiodipropionic acid (control) were dissolved in methanol and diluted in a concentration gradient. The sample solutions are shown in Table 1.

TABLE 1

Sample Solutions

| No. | Samples | Concentrations (μg/ml) |
|---|---|---|
| Vc | Vitamin C | 1.648, 8.242, 16.484, 37.969, 65.938, 131.875, 263.750, 527.500, 1055.000 |
| A | hydroxytyrosol thiodipropionic acid ester | 1.648, 8.242, 16.484, 37.969, 65.938, 131.875, 263.750, 527.500, 1055.000 |
| B | hydroxytyrosol | 1.648, 8.242, 16.484, 37.969, 65.938, 131.875, 263.750, 527.500, 1055.000 |
| C | thiodipropionic acid | 1.648, 8.242, 16.484, 37.969, 65.938, 131.875, 263.750, 527.500, 1055.000 |
| D | hydroxytyrosol and thiodipropionic acid (2:1) physical mixture | 1.648, 8.242, 16.484, 37.969, 65.938, 131.875, 263.750, 527.500, 1055.000 |

(c) Specific steps:

Measuring the scavenging activity of the sample solutions: 2 mL of the sample solutions (table 1) at each concentration gradient was taken, 2 mL $0.2 \times 10^{-4}$ mol/L DPPH solution was added, the mixture was mixed and reacted at room temperature in dark for 30 minutes, and methanol was then added to adjust final volume. The absorbance $A_i$ was measured at 517 nm. 2 mL control solution and 2 mL methanol were mixed, and the absorbance $A_j$ was measured. 2 mL DPPH solution and 2 mL methanol were mixed, and the absorbance $A_0$ was measured. The results are shown in Table 2.

Figure 3:
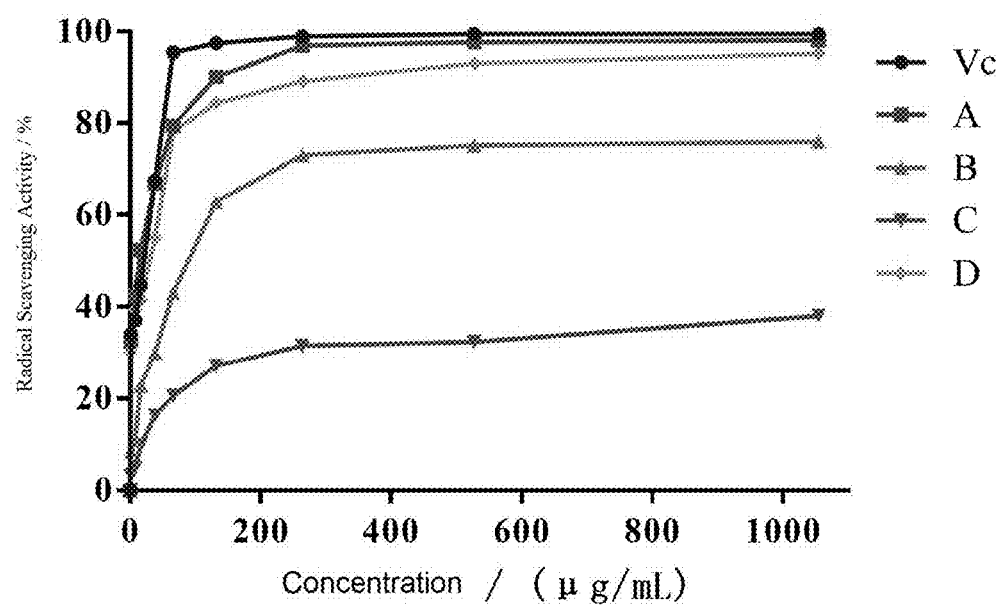
FIG. 3 shows the DPPH radical scavenging activity of the hydroxytyrosol thiodipropionic acid ester and control samples.

(d) The scavenging activity of the sample solution and control solutions is calculated according to the following calculation formula and shown in Table 3 and FIG. 3.

$$\text{Scavenging activity (\%)} = 100 \times [1-(A_i-A_j)/A_0]$$

TABLE 3

DPPH Radical Scavenging Activity

| Concentration/ | Scavenging Activity (%) (n = 3) | | | | |
|---|---|---|---|---|---|
| (μg/mL) | Vc | A | B | C | D |
| 1.648 | 34.01 | 32.44 | 8.44 | 3.24 | 30.13 |
| 8.242 | 37.06 | 42.37 | 10.97 | 4.86 | 39.30 |
| 16.484 | 44.67 | 52.29 | 22.78 | 9.72 | 41.48 |
| 37.969 | 67.51 | 66.79 | 29.96 | 16.19 | 55.02 |
| 65.938 | 95.43 | 79.39 | 43.04 | 20.65 | 78.17 |
| 131.875 | 97.46 | 90.01 | 62.87 | 27.13 | 84.28 |
| 263.750 | 98.98 | 96.95 | 73.00 | 31.58 | 89.08 |
| 527.500 | 99.49 | 97.71 | 75.11 | 32.39 | 93.01 |
| 1055.000 | 99.49 | 98.09 | 75.95 | 38.06 | 95.20 |

As shown in Table 3 and FIG. 3, hydroxytyrosol thiodipropionic acid ester (A) has obvious DPPH radical scavenging activity in a concentration dependent manner. Specifically, the DPPH radical scavenging activity ranges from 32.44% at 1.648 μg/mL to 98.09% at 1055 μg/mL. Hydroxytyrosol thiodipropionic acid ester (A) has better DPPH radical scavenging activity than hydroxytyrosol (B), thiodipropionic acid (C), and a 2:1 physical mixture of hydroxytyrosol and thiodipropionic acid (D) at same concentration. Hydroxytyrosol thiodipropionic acid ester (A) has similar DPPH radical scavenging activity to vitamin C. Accordingly, hydroxytyrosol thiodipropionic acid ester can be used a food and cosmetic antioxidant additive, and has a wide application prospect.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

TABLE 1

Absorbance

| | | Concentrations/(μg/mL) | | | | | | | | |
|---|---|---|---|---|---|---|---|---|---|---|
| Sample | Absorbance | 1.648 | 8.242 | 16.484 | 37.969 | 65.938 | 131.875 | 263.750 | 527.500 | 1055.000 |
| Vc | Ai | 0.195 | 0.190 | 0.172 | 0.124 | 0.066 | 0.056 | 0.053 | 0.064 | 0.051 |
| | Aj | 0.065 | 0.066 | 0.063 | 0.060 | 0.057 | 0.051 | 0.051 | 0.063 | 0.050 |
| | Ao | | | | | 0.197 | | | | |
| A | Ai | 0.232 | 0.214 | 0.178 | 0.153 | 0.114 | 0.085 | 0.065 | 0.053 | 0.050 |
| | Aj | 0.055 | 0.063 | 0.053 | 0.066 | 0.060 | 0.059 | 0.057 | 0.047 | 0.045 |
| | Ao | | | | | 0.262 | | | | |
| B | Ai | 0.257 | 0.252 | 0.234 | 0.197 | 0.167 | 0.135 | 0.111 | 0.128 | 0.115 |
| | Aj | 0.040 | 0.041 | 0.051 | 0.031 | 0.032 | 0.047 | 0.047 | 0.069 | 0.058 |
| | Ao | | | | | 0.237 | | | | |
| C | Ai | 0.273 | 0.266 | 0.253 | 0.242 | 0.238 | 0.224 | 0.217 | 0.223 | 0.203 |
| | Aj | 0.034 | 0.031 | 0.030 | 0.035 | 0.042 | 0.044 | 0.048 | 0.056 | 0.050 |
| | Ao | | | | | 0.247 | | | | |
| D | Ai | 0.223 | 0.198 | 0.182 | 0.168 | 0.112 | 0.102 | 0.094 | 0.078 | 0.071 |
| | Aj | 0.063 | 0.059 | 0.048 | 0.065 | 0.062 | 0.066 | 0.069 | 0.062 | 0.060 |
| | Ao | | | | | 0.229 | | | | |

What is claimed is:

1. A compound having the following formula I:

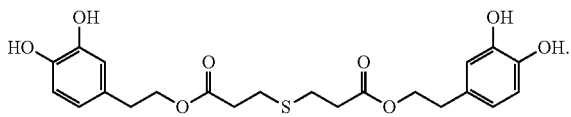

2. A method of preparing the compound of claim 1, comprising:
reacting the compound of formula II with the compound of formula III to obtain the compound of formula I:

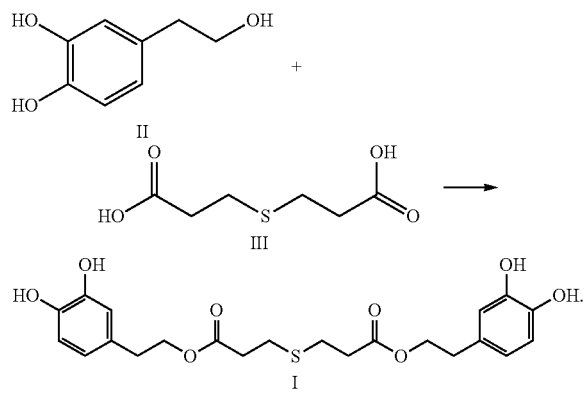

3. The method of claim 2, wherein the reaction of the compound of formula II with the compound of formula III comprises the following steps:
dissolving the compound of formula II and the compound of formula III in an organic solvent to form a reaction mixture under nitrogen atmosphere;
adding a dehydrating agent to the reaction mixture;
heating the reaction mixture at 50-60° C. for 8-10 hours under sonication;
removing the organic solvent from the reaction mixture to obtain a crude product; and
purifying the crude product on a microporous resin with a mixture of methanol and water as an eluent.

4. The method of claim 3, wherein the organic solvent is acetonitrile, THF, or DMF.

5. The method of claim 4, wherein the organic solvent is DMF.

6. The method of claim 3, wherein the molar ratio of the compound of formula II and the compound of formula III is 2:1 to 2.2:1.

7. The method of claim 6, wherein the molar ratio of the compound of formula II and the compound of formula III is 2.2:1.

8. The method of claim 3, wherein the dehydrating agent is DCC, concentrated sulfuric acid, or EDC.

9. The method of claim 8, wherein the dehydrating agent is DCC.

10. The method of claim 3, wherein the reaction mixture is heated at 60° C.

11. The method of claim 3, wherein the reaction mixture is heated for 8 hours.

12. The method of claim 3, wherein the mixture of methanol and water has a volume ratio of 1:1.

* * * * *